US012810748B2

(12) United States Patent
Moreland et al.

(10) Patent No.: US 12,810,748 B2

(45) Date of Patent: Nov. 24, 2026

(54) ILLUMINATED ANATOMICAL MODELS AND ASSOCIATED METHODS

(71) Applicant: ARTHREX, INC., Naples, FL (US)

(72) Inventors: Michael Moreland, Fort Myers, FL (US); Reinhold Schmieding, Naples, FL (US); Nick Metcalfe, Bonita Springs, FL (US); David Knopf, Bonita Springs, FL (US); Timothy Roberts, Bonita Springs, FL (US); Alyssa Morgan, Naples, FL (US); Marc Stoll, Fort Myers, FL (US)

(73) Assignee: ARTHREX, INC., Naples, FL (US)

( * ) Notice: Subject to any disclaimer, the term of this patent is extended or adjusted under 35 U.S.C. 154(b) by 123 days.

(21) Appl. No.: 18/595,608

(22) Filed: Mar. 5, 2024

(65) Prior Publication Data

US 2024/0355230 A1 Oct. 24, 2024

Related U.S. Application Data

(60) Provisional application No. 63/488,846, filed on Mar. 7, 2023.

(51) Int. Cl.

*G09B 23/30* (2006.01)
*A61B 34/10* (2016.01)
*H05B 45/00* (2022.01)

(52) U.S. Cl.

CPC .............. *G09B 23/30* (2013.01); *A61B 34/10* (2016.02); *H05B 45/00* (2020.01); *A61B 2034/105* (2016.02)

(58) Field of Classification Search

CPC ........ G09B 23/28; G09B 23/32; G09B 23/34; G09B 23/285

See application file for complete search history.

(56) References Cited

U.S. PATENT DOCUMENTS

| | | | |
|---|---|---|---|
| 5,997,307 | A | 12/1999 | LeJune, Jr. |
| 6,544,041 | B1 | 4/2003 | Damadian |
| 6,780,016 | B1 | 8/2004 | Toly |
| 7,931,471 | B2 | 4/2011 | Senagore et al. |
| 8,439,687 | B1 | 5/2013 | Morriss et al. |

(Continued)

FOREIGN PATENT DOCUMENTS

| | | |
|---|---|---|
| CN | 108198497 | 6/2018 |
| CN | 208706118 | 4/2019 |

(Continued)

OTHER PUBLICATIONS

International Preliminary Report on Patentability for International Application No. PCT/US2024/018483 mailed Sep. 18, 2025.

(Continued)

*Primary Examiner* — Robert J Utama

(74) *Attorney, Agent, or Firm* — Carlson, Gaskey & Olds, P.C.

(57) ABSTRACT

This disclosure relates to surgical systems, devices and methods for planning and implementing surgical procedures. The systems and methods disclosed herein may be utilized to establish physical anatomical models of anatomy. One or more light sources may be configured to illuminate the physical anatomical models.

20 Claims, 12 Drawing Sheets

(56) References Cited

U.S. PATENT DOCUMENTS

| | | | | |
|---|---|---|---|---|
| 8,827,720 | B1 * | 9/2014 | Lazarus | G09B 23/32 434/262 |
| 9,183,764 | B2 | 11/2015 | Sugimoto et al. | |
| 9,805,624 | B2 | 10/2017 | Reihsen et al. | |
| 9,842,515 | B1 | 12/2017 | TenBrink | |
| 10,290,236 | B2 | 5/2019 | Bernal | |
| 10,354,556 | B2 | 7/2019 | Hofstetter | |
| 10,769,966 | B2 | 9/2020 | Sebro | |
| 10,796,606 | B2 | 10/2020 | Felsinger et al. | |
| 10,957,221 | B2 | 3/2021 | Kerins et al. | |
| 2007/0148626 | A1 | 6/2007 | Ikeda | |
| 2014/0370477 | A1 | 12/2014 | Black et al. | |
| 2015/0339954 | A1 * | 11/2015 | East | A61B 17/1671 434/274 |
| 2016/0104394 | A1 | 4/2016 | Miyazaki | |
| 2020/0043371 | A1 | 2/2020 | Mele et al. | |
| 2020/0118465 | A1 | 4/2020 | Hoppmann et al. | |
| 2020/0349864 | A1 | 11/2020 | Hanna | |
| 2021/0248926 | A1 | 8/2021 | Welch et al. | |

FOREIGN PATENT DOCUMENTS

| | | |
|---|---|---|
| EP | 1677273 | 7/2006 |
| JP | 2001005377 | 1/2001 |
| JP | 2015082043 | 4/2015 |
| JP | 2016168078 | 9/2016 |
| JP | 2017068413 | 4/2017 |
| JP | 2018153626 | 10/2018 |
| JP | 2019048044 | 3/2019 |
| JP | 2026501870 | 1/2026 |
| RU | 2129306 | 4/1999 |
| WO | 2019158470 | 8/2019 |
| WO | 2022037748 | 2/2022 |
| WO | 2022250834 | 12/2022 |

OTHER PUBLICATIONS

International Search Report and Written Opinion for International Application No. PCT/US2024/018483 mailed May 27, 2024.

New Zealand Examination Report for New Zealand Patent Application No. 824821 mailed Oct. 21, 2025.

Australian Examination Report for Australian Patent Application No. 2024232867 mailed Nov. 5, 2025.

Neijhoft, J., Henrich, D., Mors, K., Marzi, I. & Janko, M. (2022). Visualization of complicated fractures by 3D-printed models for teaching and surgery: hands-on transitional fractures fo the ankle. European Journal of Trauma and Emergency Surgery/ 2022. pp. 2-11.

Bach, M., Aberle, C., Depeursinge, A., Jimenez-Del-Toro, O., Schaer, R., Flouris, K., Konukoglu, E., Muller, H., Stleltjes, B. & Obmann, M.M. (2023). 3D-printed iodine-ink CT phantom for radiomics feature extraction—advantages and challenges. Medical Physics. 2023. vol. 50. pp. 5682-5697.

Notice of Reasons for Rejection for Japanese Application No. 2025-552002 mailed Mar. 10, 2026.

European Office Action for European Patent Application No. 24717844.5 mailed Mar. 5, 2026.

Communication pursuant to Article 94(3) for European Patent Application No. 24717844.5 mailed Aug. 17, 2026.

* cited by examiner

ILLUMINATED ANATOMICAL MODELS AND ASSOCIATED METHODS

CROSS REFERENCE TO RELATED APPLICATION

The present disclosure claims the benefit of U.S. Provisional Application No. 63/488,846 filed Mar. 7, 2023, incorporated herein by reference in its entirety.

BACKGROUND

This disclosure relates to surgical systems, devices and methods for planning and implementing surgical procedures utilizing physical models of anatomy.

Deformities may form along various bones and joints of the human musculoskeletal system. Surgeons may prepare for surgery by performing a procedure on a cadaveric or saw bone specimen.

SUMMARY

This disclosure relates to systems, devices and methods of performing a surgical procedure. The systems may be utilized for performing one or more surgical procedures on physical models representative of anatomy.

A system for a surgical procedure according to an implementation may include a physical anatomical model including a main body representative of anatomy. The main body may include one or more bone components each having a surface contour representative of a respective bone. The main body may include one or more soft tissue components on the one or more bone components. The one or more soft tissue components may be representative of soft tissue and may be transparent or translucent. A light source may be embedded in the main body.

A physical anatomical model for a surgical procedure according to an implementation may include an opaque bone component representative of bone. A transparent or translucent soft tissue component may be representative of soft tissue. The soft tissue component may be disposed along a circumference of the bone component. A light source may be between the bone component and the soft tissue component. The light source may include a plurality of light modules that may be distributed about the circumference of the bone component.

A training system for a surgical procedure according to an implementation may include a physical anatomical model including a main body representative of an anatomy. An imaging fixture may be dimensioned to engage an imaging device such that the imaging device may face the physical anatomical model.

A method of rehearsing for a surgical procedure according to an implementation may include defining a virtual anatomical model associated with an anatomy. The method may include forming a plurality of layers of material to establish a physical anatomical model representative of the virtual anatomical model. The layers of material may establish a main body. The main body may include a bone component having a surface contour representative of a bone. The bone component may include opaque material. The main body may include a soft tissue component representative of soft tissue. The soft tissue component may include transparent or translucent material. The method may include embedding a light source in the main body.

The present disclosure may include any one or more of the individual features disclosed above and/or below alone or in any combination thereof.

The various features and advantages of this disclosure will become apparent to those skilled in the art from the following detailed description. The drawings that accompany the detailed description can be briefly described as follows.

BRIEF DESCRIPTION OF THE DRAWINGS

Like reference numbers and designations in the various drawings indicate like elements.

DETAILED DESCRIPTION

Figure 1:
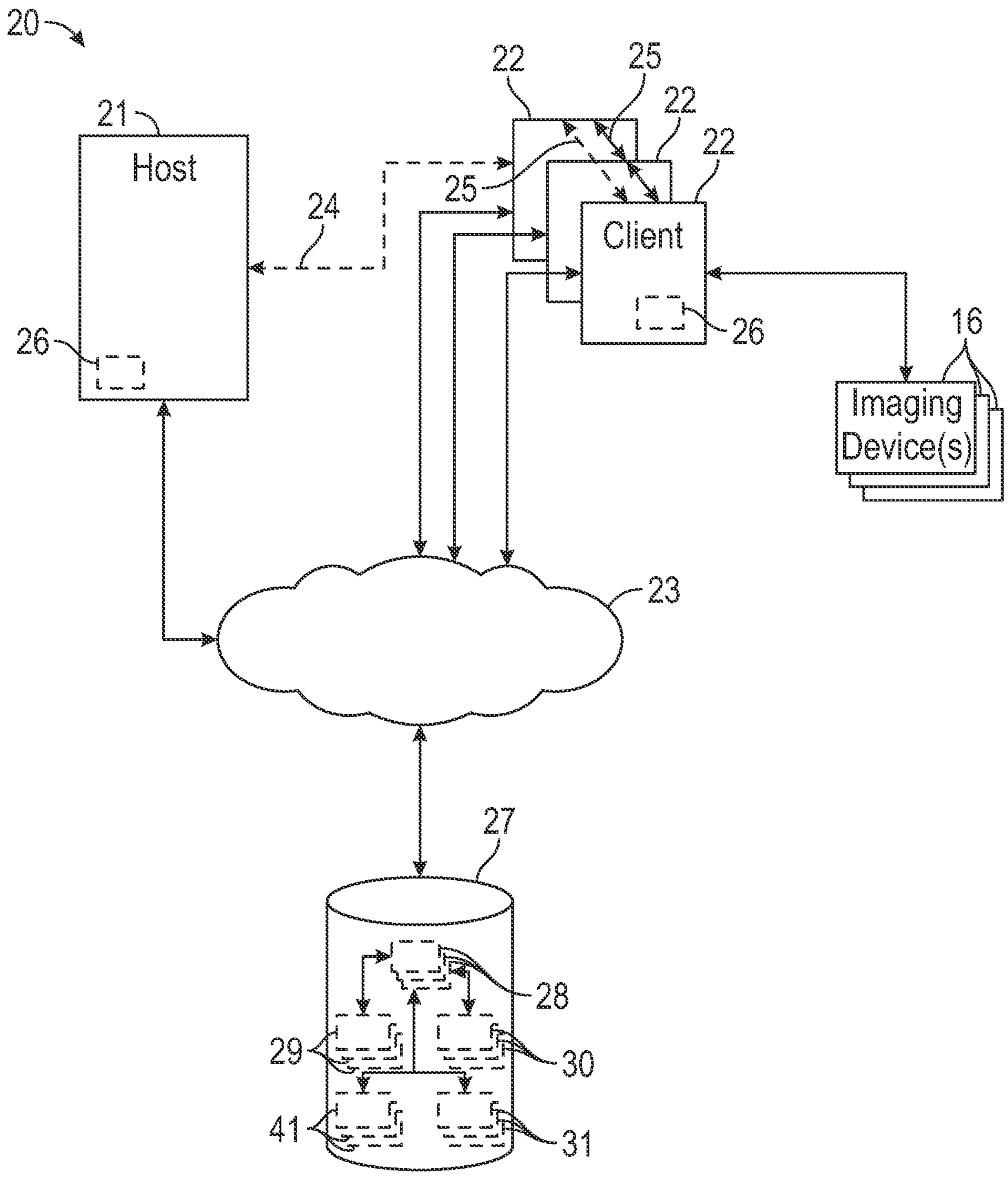
FIG. 1 discloses a planning system.

This disclosure relates to surgical systems, devices and methods for planning and implementing surgical procedures utilizing physical models of anatomy. Physical anatomical models may be utilized to rehearse and train for various surgical procedures.

The disclosed techniques may be utilized to provide the surgeon a training experience that may be targeted or tailored to the surgeon based on skill set, experience, etc. The surgeon may select a particular configuration of a virtual anatomical model that may be fabricated or otherwise formed to establish a physical anatomical model based on the anatomy or pathology that the surgeon may intend to treat. In scenarios, the surgeon may not be familiar with a particular deformity and may choose to train utilizing that configuration of the physical anatomical model. The surgeon may utilize the physical anatomical model to train with particular instrumentation, implants and other devices that may be intended for a planned surgery. Once training on the physical anatomical model is completed, the surgeon may select a more challenging case in a subsequent training cycle. Unlike cadaveric and saw bone specimens, the physical anatomical model may be associated with a specific patient which may improve the ability to determine how well the surgeon actually performed the surgical procedure with respect to the intended anatomy.

The surgeon, assistant or other user may interact with a graphical user interface (GUI) to select various parameters or characteristics of the physical anatomical model. The parameters may include anatomy, joint type, tissue type, bone density, defect type, color scheme, etc., to establish a desired configuration of the physical anatomical model. The surgeon may tailor or select one or more variables or parameters specific to a patient, depending on what the surgeon would like to train. The specified parameters may be represented in the physical anatomical model.

The surgeon may interact with the user interface to select a desired case associated with a respective virtual anatomical model. The surgeon may interact with the user interface to review prior cases, such as the case of a particular esteemed surgeon which may be recognized as the "gold standard" for a respective procedure. The surgeon may select a case corresponding to an intended patient or may select a case that may closely correspond to a particular classification.

The physical anatomical model may incorporate one or more light sources for illuminating the physical anatomical model. The light sources may be configured to selectively highlight various components of the physical anatomical model, such as bone components representative of various bones and/or soft tissue components representative of various soft tissue. The illumination may assist the surgeon in performing a procedure and/or evaluating the physical anatomical model. An imaging device may capture modifications to the physical anatomical model. The modifications may be compared to a surgical plan for providing feedback to the surgeon.

A system for a surgical procedure according to an implementation may include a physical anatomical model including a main body representative of anatomy. The main body may include one or more bone components each having a surface contour representative of a respective bone. The main body may include one or more soft tissue components on the one or more bone components. The one or more soft tissue components may be representative of soft tissue and may be transparent or translucent. A light source may be embedded in the main body.

In implementations, the light source may be at least partially embedded in the one or more bone components.

In implementations, the light source may be situated between the one or more bone components and the one or more soft tissue components.

In implementations, the light source may include first and second modes associated with first and second frequency ranges, respectively. The one or more bone components may include a first material that may be responsive to light in the first frequency range, but not the second frequency range. The one or more soft tissue components may include a second material that may be responsive to light in the second frequency range, but not the first frequency range.

In implementations, the light source may include a first light module and a second light module that may be spaced apart from the first light module. The first and second light modules may be independently controllable.

In implementations, the main body may extend along a first axis. The first light module may extend along a first reference plane that may extend along the first axis. The second light module may extend along a second reference plane that may extend along the first axis. The first and second reference planes may be circumferentially offset to establish an angle.

In implementations, the first light module and/or the second light module may include an array of light emitting diodes that may be distributed along a respective one of the first and second reference planes.

In implementations, the angle may be approximately 90 degrees or more.

In implementations, the first reference plane may be associated with an anterior-posterior view of the physical anatomical model. The second reference plane may be associated with a lateral view of the physical anatomical model.

In implementations, at least one indicator may be embedded in the main body. The at least one indicator may be adapted to selectively illuminate in response to the light source.

A physical anatomical model for a surgical procedure according to an implementation may include an opaque bone component representative of bone. A transparent or translucent soft tissue component may be representative of soft tissue. The soft tissue component may be disposed along a circumference of the bone component. A light source may be between the bone component and the soft tissue component. The light source may include a plurality of light modules that may be distributed about the circumference of the bone component.

In implementations, the plurality of light modules may be independently controllable.

In implementations, the plurality of light modules may include a pair of light modules that may be circumferentially offset at angle of approximately 90 degrees or more relative to an axis of the bone component.

A training system for a surgical procedure according to an implementation may include a physical anatomical model including a main body representative of an anatomy. An imaging fixture may be dimensioned to engage an imaging device such that the imaging device may face the physical anatomical model.

In implementations, the imaging fixture may include one or more receptacles dimensioned to engage the imaging device.

In implementations, the one or more receptacles may be a plurality of slots that may be arranged at predefined orientations relative to each other.

In implementations, a mount may be attached to the main body. The mount may be adapted to releasable secure the physical anatomical model to a positioning fixture.

A method of rehearsing for a surgical procedure according to an implementation may include defining a virtual anatomical model associated with an anatomy. The method may include forming a plurality of layers of material to establish a physical anatomical model representative of the virtual anatomical model. The layers of material may establish a main body. The main body may include a bone component having a surface contour representative of a bone. The bone component may include opaque material. The main body may include a soft tissue component representative of soft tissue. The soft tissue component may include transparent or translucent material. The method may include embedding a light source in the main body.

In implementations, the layers of material may have respective moduli of elasticity that may substantially correspond to moduli of elasticity of respective portions of the anatomy.

In implementations, the method may include actuating the light source in a first mode to highlight the bone component, but actuating the light source in a second mode to highlight the soft tissue component. The first and second modes may be associated with different frequencies.

In implementations, the light source may include a first light module and a second light module. The method may include independently actuating the first light module and the second light module to illuminate respective regions of the main body.

In implementations, the main body may extend along a first axis. The first light module and the second light module may be circumferentially offset from each other relative to the first axis.

In implementations, the method may include positioning the physical anatomical model relative to an imaging fixture. The method may include positioning an imaging device in the imaging fixture. The method may include modifying the physical anatomical model. The method may include causing the imaging device to capture one or more images of the modified physical anatomical model when illuminated by the light source.

In implementations, the method may include comparing the one or more images of the modified physical anatomical model to another instance of a virtual anatomical model. The method may include generating an indicator in response to the comparing step.

FIG. 1 illustrates a planning system 20 that may be utilized for planning surgical procedures according to an implementation. The system 20 may be used for planning orthopaedic procedures, including pre-operatively, intra-operatively and/or post-operatively to create, edit, execute and/or review surgical plans. The system 20 may be used for training and rehearsing for various surgical procedures, including prior cases and surgical plans for patients and hypothetical cases.

The system 20 may include a host computer 21 and one or more client computers 22. The host computer 21 may be configured to execute one or more software programs. In implementations, the host computer 21 may include more than one computer jointly configured to process software instructions serially or in parallel.

The host computer 21 may be in communication with one or more networks such as a network 23 comprised of one or more computing devices. The network 23 may be a private local area network (LAN), a private wide area network (WAN), the Internet, or a mesh network.

The host computer 21 and each client computer 22 may include one or more of a computer processor, memory, storage means, network device and input and/or output devices and/or interfaces. The input devices may include a keyboard, mouse, etc. The output device may include a monitor, speakers, printers, etc. The memory may include UVPROM, EEPROM, FLASH, RAM, ROM, DVD, CD, a hard drive, or other computer readable medium which may store data and/or other information relating to the features and techniques disclosed herein. The host computer 21 and each client computer 22 may be a desktop computer, laptop computer, smart phone, tablet, or any other computing device. The interface may facilitate communication with the other systems and/or components of the network 23.

Each client computer 22 may be configured to communicate with the host computer 21 directly via a direct client interface 24 or over the network 23. The client computers 22 may be configured to execute one or more software programs, such as various surgical tools. Each client computer 22 may be operable to access and locally and/or remotely execute a planning environment 26. The planning environment 26 may be a standalone software package or may be incorporated into another surgical tool.

The planning environment 26 may be configured to communicate with the host computer 21 either over the network 23 or directly through the direct client interface 24. In implementations, the client computers 22 may be configured to communicate with each other directly via a peer-to-peer interface 25.

The planning environment 26 may provide a display or visualization of one or more virtual anatomical models 29 and related images and/or one or more implant models 30 via one or more graphical user interfaces (GUI). Each anatomical model 29, implant model 30, and related images and other information may be stored in one or more files or records according to a specified data structure.

The system 20 may include at least one storage system 27, which may be operable to store or otherwise provide data to other computing devices. The storage system 27 may be a storage area network device (SAN) configured to communicate with the host computer 21 and/or the client computers 22 over the network 23. In implementations, the storage system 27 may be incorporated within or directly coupled to the host computer 21 and/or client computers 22. The storage system 27 may be configured to store one or more of computer software instructions, data, database files, configuration information, etc.

In implementations, the system 20 may be a client-server architecture configured to execute computer software on the host computer 21, which may be accessible by the client computers 22 using either a thin client application or a web browser executing on the client computers 22. The host computer 21 may load the computer software instructions from local storage, or from the storage system 27, into memory and may execute the computer software using the one or more computer processors.

The system 20 may include one or more databases 28. The databases 28 may be stored at a central location, such as the storage system 27. In implementations, one or more databases 28 may be stored at the host computer 21 and/or may be a distributed database provided by one or more of the client computers 22. Each database 28 may be a relational database configured to associate one or more anatomical models 29 and/or one or more implant models 30 to each other and/or a surgical plan 31. Each surgical plan 31 may be associated with a respective patient. Each anatomical model 29, implant model 30 and surgical plan 31 may be assigned a unique identifier or database entry. The database 28 may be configured to store data corresponding to the anatomical models 29, implant models 30 and surgical plans 31 in one or more database records or entries, and/or may be configured to link or otherwise associate one or more files corresponding to each respective anatomical model 29, implant model 30 and surgical plan 31. Anatomical models 29 stored in the database(s) 28 may correspond to respective patient anatomies from prior and/or planned surgical cases, and may be arranged into one or more predefined categories such as sex, age, ethnicity, size, defect category, procedure type, etc. The anatomical models 29 and/or implant models 30 may be associated with respective instrumentation and devices to implement the associated surgical plan 31.

The system 10 may include or interface with one or more imaging devices 16. Each client computer 22 and/or host 21 computer may be coupled to one or more of the imaging devices 16. Each imaging device 16 may be configured to capture or acquire one or more images 41 associated with anatomy residing within a scan field (e.g., window) of the imaging device 16. The imaging device 16 may be configured to capture or acquire two dimensional (2D) and/or three dimensional (3D) greyscale and/or color images. Various imaging devices 16 may be utilized, including but not limited to an X-ray machine, a computerized tomography (CT) machine, or a magnetic resonance imaging (MRI) machine, for obtaining one or more images of a patient. The imaging devices 16 may include mobile devices such as a personal computer (e.g., laptop or tablet), cellular phone or digital camera. The planning environment 28 may be configured to interact with one or more of the imaging devices 16 to capture or acquire the images 41.

Each anatomical model 29 may include information obtained from one or more medical devices or tools, including any of imaging devices disclosed herein, that may obtain one or more images of patient anatomy. The anatomical model 29 may include one or more digital images and/or coordinate information relating to an anatomy of the patient obtained or derived from the medical device(s). In implementations, one or more of the anatomical models 29 may be created by a designer and may represent a hypothetical anatomy. Each implant model 30 may include coordinate information associated with a predefined design. The planning environment 26 may incorporate and/or interface with one or more modeling packages, such as a computer aided design (CAD) package, to render the models 29, 30 as two-dimensional (2D) and/or three-dimensional (3D) volumes or constructs. Each anatomical model 29 and implant model 30 may correspond to 2D and/or 3D geometry, and may be utilized to generate a wireframe, mesh and/or solid construct in a display.

The implant models 30 may correspond to implants and components of various configurations, shapes, sizes, procedures, instrumentation, etc. Each implant may include one or more components that may be situated at a surgical site including plates, anchors, screws, nails, suture, grafts, etc. Each implant model 30 may correspond to a single component or may include two or more components that may be configured to establish an assembly. The implant models 30 may include base plates coupled to an articulation member, bone plates configured to interconnect adjacent bones or bone fragments, intermedullary nails, suture anchors, etc. The articulation member may have an articular surface dimensioned to mate with an articular surface of an opposed bone or implant.

Each surgical plan 31 may be associated with one or more of the anatomical models 29 and/or implant models 30. The surgical plan 31 may include one or more revisions to the anatomical model 29 and information relating to a position of an implant model 30 relative to the original and/or revised anatomical model 29. The surgical plan 31 may include coordinate information relating to the revised anatomical model 29 and a relative position of the implant model 30 in predefined data structure(s). Revisions to each anatomical model 29, implant model 30 and surgical plan 31 may be stored in the database 28 automatically and/or in response to user interaction with the system 20.

One or more surgeons, assistants and other clinical users may be provided with a planning environment 26 via the client computers 22 and may simultaneously access each anatomical model 29, implant model 30 and surgical plan 31 stored in the database(s) 28. Each user may interact with the planning environment 26 to create, view and/or modify various aspects of the surgical plan 31. Each client computer 22 may be configured to store local instances of the anatomical models 29, implant models 30 and/or surgical plans 31, which may be synchronized in real-time or periodically with the database(s) 28. The planning environment 26 may be a standalone software package executed on a client computer 22 or may be provided as one or more services executed on the host computer 21.

Figure 2:
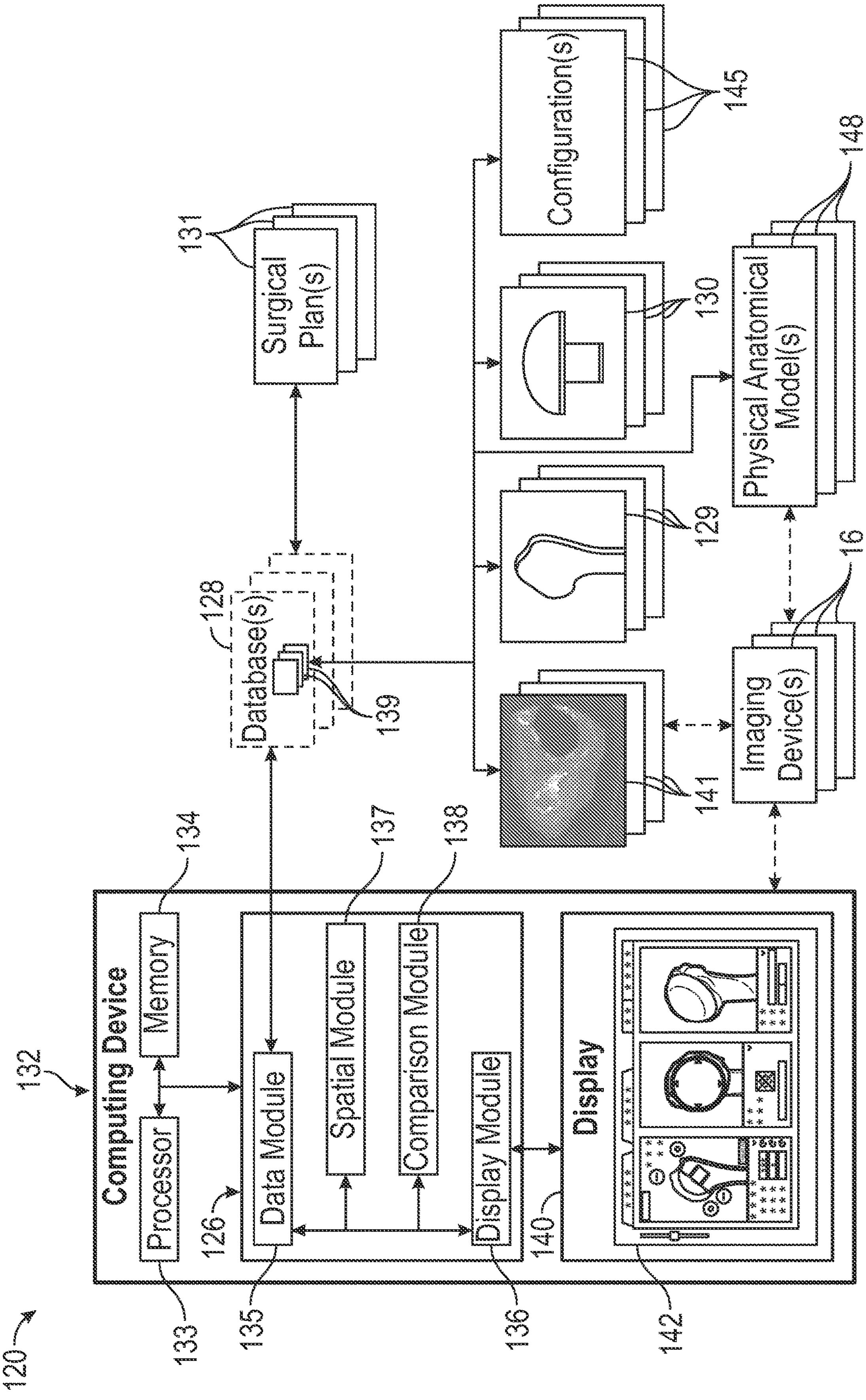
FIG. 2 discloses another planning system including a user interface.

FIG. 2 illustrates a surgical system 120 according to an implementation. The system 120 be utilized to facilitate planning, rehearsing and/or training for a surgical procedure. The system 120 may be utilized to plan, rehearse, train and implement various orthopaedic and other surgical procedures, such as an arthroplasty to repair a joint. The system 120 may be utilized in planning a resection or revision of one or more bones. The system 120 may be utilized in planning placement of an implant to restore functionality to a bone and/or joint. The planning system 120 may be utilized in the repair of various locations of the patient and surgical procedures including repair of joints such as a shoulder, foot, ankle, wrist, hand, hip or knee, and including repair of other tissue such as cartilage, muscles, tendons and ligaments.

The system 120 may be configured to generate one or more physical anatomical models 148, including any of the physical anatomical models disclosed herein. The surgeon may perform one or more modifications to the physical anatomical model 148 to rehearse or train for a surgical procedure. The system 120 may be configured to generate configuration(s) 145 associated with respective physical anatomical model(s) 148. The configuration 145 may be utilized in the formation of a physical anatomical model 148. Each physical anatomical model 148 may be representative of a virtual anatomical model 129, including a substantially or generally corresponding geometry, texture, density, porosity, color, etc. as the virtual anatomical model 129. The virtual anatomical model 129 may be associated with an anatomy, such as the anatomy of a patient and/or a hypothetical anatomy. The anatomical models 129 may include one or more anatomical features. The anatomical features may be representative of anatomy, including one or more bones including cartilage, cortical and/or cancellous bone tissue, soft tissue including muscle, ligaments and/or tendons, etc., and/or other tissue.

The system 120 may include a computing device 132. The computing device 132 may include at least one processor 133 coupled to memory 134. The computing device 132 may include any of the computing devices disclosed herein, such as the host computer 21 and/or client computer 22 of FIG. 1. The processor 133 may be configured to execute a planning environment 126 for creating, editing, executing and/or reviewing one or more surgical (e.g., pre-operative) plans 131 during pre-operative, intra-operative and/or post-operative phases of a surgical procedure. The processor 133 may be configured to access one or more virtual anatomical models 129 from a storage location such as the memory 134. The anatomical model 129 and surgical plan 131 may be associated with an actual case for a patient or may be a hypothetical case established for rehearsal and/or training surgeons, assistants, medical staff and other clinical users.

The planning environment 126 may include at least a data module 135, display module 136, spatial module 137 and comparison module 138. The processor 133 may be configured to execute the data module 135, display module 136, spatial module 137 and comparison module 138. Although four modules are disclosed in the implementation of FIG. 2, it should be understood that fewer or more than four modules may be utilized and/or one or more of the modules may be combined to provide the disclosed functionality.

The data module 135 may be configured to access, retrieve and/or store data and other information in the database(s) 128 corresponding to one or more images 141, virtual anatomical model(s) 129, implant model(s) 130 and/or surgical plan(s) 131. The data and other information may be stored in the database 128 as one or more records or entries 139. In implementations, the data and other information may be stored in one or more files that may be accessible by referencing one or more objects or memory locations referenced by the records 139.

The data module 135 may be configured to receive data and other information corresponding to at least one or more images 141, physical anatomical models 148, etc. from various sources, such as the imaging device(s) 16. The data module 135 may be further configured to command the imaging device 16 to capture or acquire the images 141 automatically or in response to user interaction.

The memory 134 may be configured to access, load, edit and/or store instances of one or more anatomical models 129, implant models 130 and/or surgical plans 131 in response to one or more commands from the data module 135. The data module 135 may be configured to cause the memory 134 to store a local instance of the anatomical model(s) 129, implant model(s) 130 and/or surgical plan(s) 131 which may be synchronized with records 139 in the database(s) 128.

The display module 136 may be configured to display data and other information relating to one or more surgical plans 131 in at least one graphical user interface (GUI) 142. The computing device 132 may be coupled to a display device 140. The display module 136 may be configured to cause the display device 140 to display the virtual anatomical model 129 in the user interface 142. A surgeon or other clinical user may interact with the user interface 142 via the planning environment 126 to create, edit and/or review aspects of one or more anatomical models 129. The surgeon or other user may interact with the user interface 142 via the planning environment 126 to create, edit, execute and/or review aspects of one or more surgical plans 131.

Each surgical plan 131 may be associated with one or more (e.g., original) virtual anatomical models 129 prior to any revisions, which may substantially or generally approximate an anatomy. Each surgical plan 131 may be associated with one or more (e.g., revised or modified) virtual anatomical models 129 that may incorporate one or more revisions or modifications to the anatomy and/or an associated physical anatomical model. The original and revised anatomical models 129 may be associated with each other in the surgical plan 131. In implementations, the revisions may be stored as one or more parameters of the original anatomical model 129.

The planning system 120 may be configured to generate a link to a surgical plan 131. The surgeon, assistant or other clinical user may interact with the link to review and edit the surgical plan 131. Interacting with the link may cause the planning system 120 to display or otherwise present aspects of the surgical plan 131 in the graphical user interface 142.

The planning system 120 may be utilized to establish one or more physical anatomical models 148, including any of the physical anatomical models disclosed herein. The physical anatomical model 148 may be representative of an associated virtual anatomical model 129. The imaging devices 16 may be utilized to capture one or more images 141 of the physical anatomical models 148 prior to, during and/or subsequent to any modifications. The system 120 may be configured to associate the images 141 with the physical anatomical model 148, including in the database 128.

Figure 3:
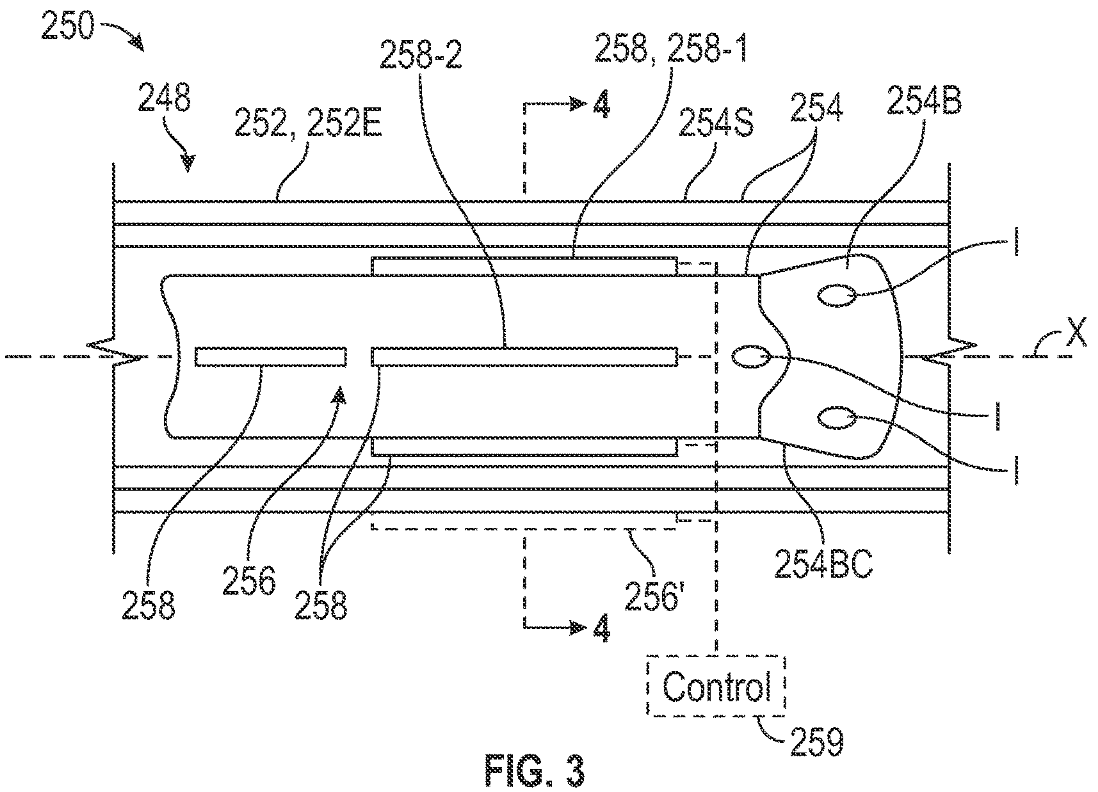
FIG. 3 discloses a system for a surgical procedure including a physical anatomical model.
Figure 4:
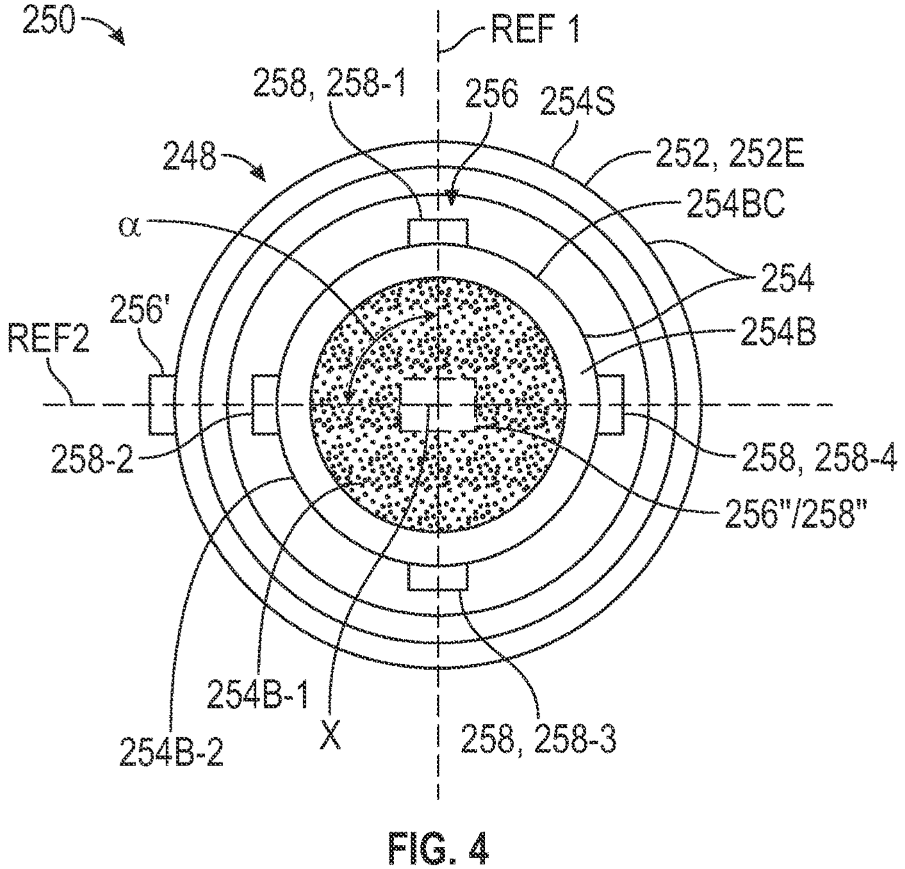
FIG. 4 discloses a sectional view of the system taken along line 4-4 of FIG. 3.

FIGS. 3-4 disclose a system 250 for a surgical procedure according to an implementation. The system 250 may include a physical anatomical model 248. The physical anatomical model 248 may include a main body 252. The main body 252 may be representative of an anatomy, such as one or more bones and/or joints including any of those disclosed herein. The main body 252 may include an external surface contour 252E. The main body 252 may include one or more components (e.g., anatomical features) 254. The components 254 may be representative of anatomy, including one or more bones including cartilage, cortical and/or cancellous bone tissue, soft tissue including muscle, ligaments and/or tendons, etc., and/or other tissue.

The components 254 may include one or more bone components 254B representative of a respective bone and/or one or more soft tissue components 254S representative of soft tissue. In implementations, the bone component 254B may be representative of a metatarsal or other bone of a foot. The metatarsal may be associated with a bunion or other deformity. Each bone component 254B may have a surface contour 254BC representative of the respective bone. The bone component 254B may include a first portion 254B-1 establishing the surface contour 254BC and a second portion 254B-2 embedded in the first portion 254B-2 (FIG. 4). The first portion 254B-1 may be representative of cortical bone. The second portion 254B-2 may be representative of cancellous bone. The soft tissue component 254S may be disposed about and/or otherwise along a circumference of the bone component 254B.

The main body 252 may extend along a (e.g., first) axis X. The axis X may be a longitudinal axis extending along a length of the main body 252. The bone component 254B may extend along the axis X of the main body.

The components 254 may be formed of any of the materials disclosed herein, including opaque, translucent and/or transparent materials. In implementations, the bone component 254B may be translucent or substantially opaque. The soft tissue component 254S may be translucent or substantially transparent. For the purposes of this disclosure, the term "substantially" means±10 percent of the stated value or relationship unless otherwise indicated. The bone components 245B may be formed from a substantially rigid material, such as a polymeric material, including photopolymers, silicones and thermoplastics. The soft tissue components 254S may be formed from a relatively flexible material, including an elastomeric material such as rubber or silicone.

The system 250 may include a light source 256 for illuminating the physical anatomical model 248. The light source 256 may be embedded in the main body 252 of the physical anatomical model 248. The light source 256 may be situated between the bone component(s) 254B and soft tissue component(s) 254S. In other implementations, light source 256' may be external to the main body 252 (shown in dashed lines). Various light sources may be utilized to illuminate the physical anatomical models disclosed herein, including incandescent, fluorescent, halogen, and/or light emitting diodes (LED). The light source 256 may be coupled to a power supply. The power supply may be external or may be embedded in the physical anatomical model (e.g., battery powered).

The light source 256 may be configured to generate light in one or more frequencies and/or frequency ranges of visible and/or non-visible light. The frequencies and/or frequency ranges may be defined in a visual light spectrum (e.g., 400 nm to 700 nm), near infrared light spectrum (e.g., 2.5 μm to 750 nm) and/or infrared light spectrum (e.g., 25 μm to 2.5 μm). The light source 256 may be configured to generate light characterized by various hue, saturation and/or brightness.

The light source 256 may include a plurality of modes associated with distinct frequencies and/or frequency ranges of visible and/or non-visible light. The plurality of modes may include first and second modes associated with first and second frequency ranges, respectively. The components 254 may incorporate materials responsive to one or more of the frequencies and/or frequency ranges such that the components 254 may be independently and distinctly illuminated from each other. In implementations, the bone component(s) 254B may include a first material responsive to light in the first frequency range, but not the second frequency range. The soft tissue component(s) 254S may include a second material responsive to light in the second frequency range, but not the first frequency range.

The physical anatomical model 248 may include one or more indicators I (FIG. 3). The indicator I may be embedded in the main body 252. The indicators I may be associated with one or more predetermined target zones and/or warning zones associated with a surgical procedure and/or surgical plan. The indicators I may be representative of one or more fracture paths associated with a bone fracture. The indicators I may be adapted to selectively illuminate in response to the light source 256, including any of the frequencies and/or frequency ranges disclosed herein, to assist the surgeon or clinical user in performing a surgical procedure.

The light source 256 may include one or more light modules 258. The light modules 258 may be spaced apart from each other. The light modules 258 may follow a contour of the adjacent component(s) 254, such as the surface contour 254BC of the bone component 254B. In implementations, light module(s) 258" may be at least partially embedded in the bone component(s) 254B (FIG. 4). The light modules 258 may be independently controllable. The system 250 may include a control 259 (FIG. 3). The control 259 may be electrically coupled to each of the light modules 258. The control 259 may be configured to independently control the light modules 258. The light modules 258 may be distributed about the circumference of the bone component 254B relative to the axis X. The light source 256 may include one or more pairs of light modules 258 such as a first light module 258-1 and a second light module 258-2 spaced apart from the first light module 258-1. The first and second light modules 258-1, 258-2 may be independently controllable.

Referring to FIG. 4, with continuing reference to FIG. 3, the first light module 258-1 may extend along a first reference plane REF1. The second light module 258-2 may extend along a second reference plane REF2. The first and/or second reference planes REF1, REF2 may extend along the axis X of the main body 252. The first and second reference planes REF1, REF2 may be circumferentially offset to establish an angle α. The angle α may be acute, perpendicular or obtuse. In implementations, the angle α may be approximately 90 degrees or more. The first and second light modules 258-1, 258-2 may be circumferentially offset at an angle α of approximately 90 degrees or more relative to an axis of the bone component 254B and/or the axis X of the main body 252.

In implementations, the system 250 may include third and fourth light modules 258-3, 258-4. The third light module 258-3 may extend along the first reference plane REF1. The fourth light module 258-4 may extend along the second reference plane REF1. The first and third light modules 258-1, 258-3 may be positioned on opposite sides of the bone component 254B. The second and fourth light modules 258-2, 258-4 may be positioned on opposite sides of the bone component 254B. The position of the light modules 258 may be associated with different planes of the anatomy (e.g., anterior-posterior, lateral, superior-inferior). The control 259 may selectively actuate the light modules 258 to highlight the associated planes of the physical anatomical model 248. In implementations, the first reference plane REF1 may be associated with an anterior-posterior view of the physical anatomical model 248. The second reference plane REF2 may be associated with a lateral view of the physical anatomical model 248.

One or more of the light modules 258 may include an array of light emitting diodes (LED) distributed along a respective one of the first and second reference planes REF1, REF2. In implementations, the first light module 258-1 and/or the second light module 258-2 may include an array of LEDs distributed along the respective one of the first and second reference planes REF1, REF2.

Figure 5:
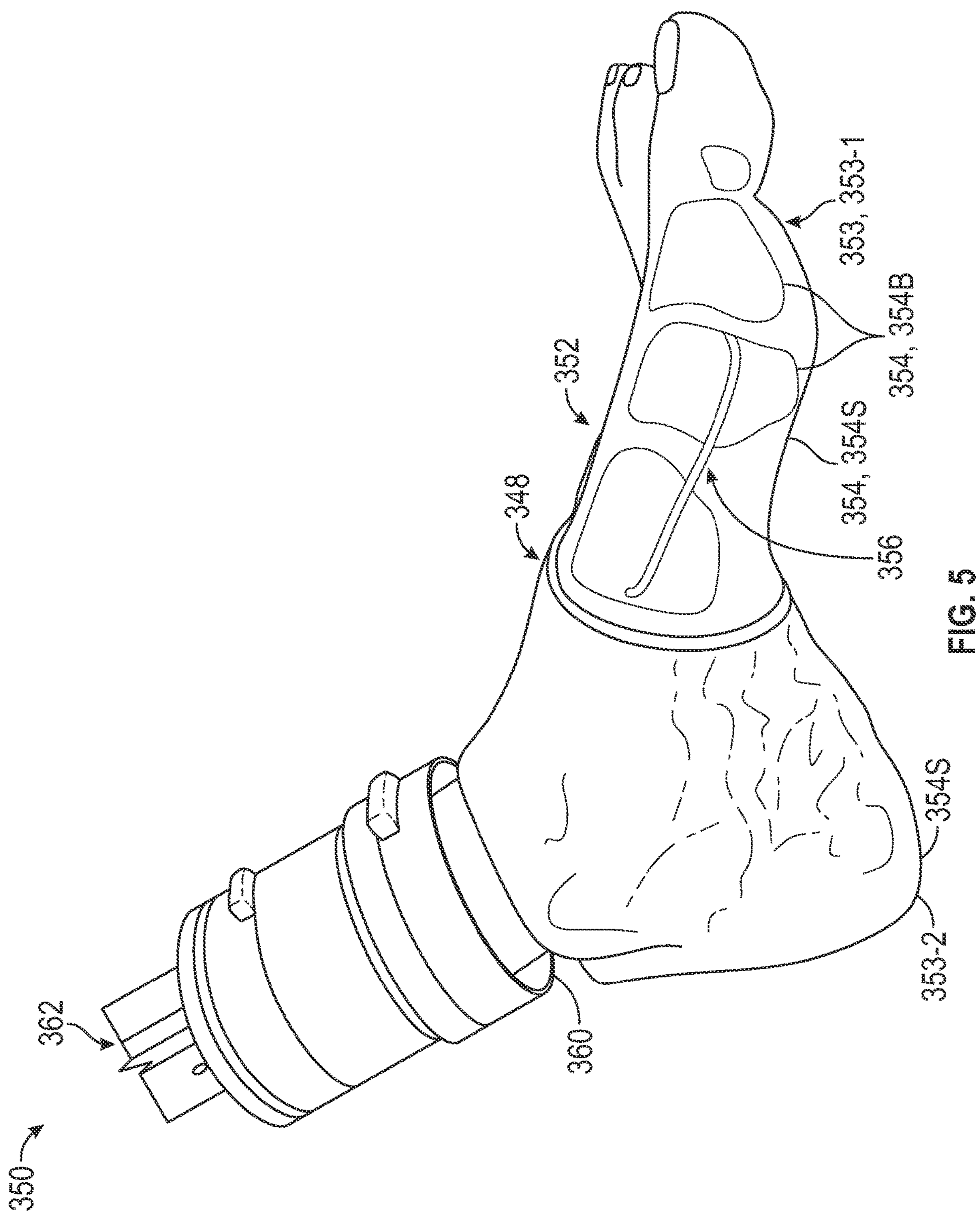
FIG. 5 discloses a perspective view of another system for a surgical procedure including a physical anatomical model, a light source in a non-illuminated mode, and the physical anatomical model connected to a positioning fixture.

FIG. 5 discloses a (e.g., training) system 350 for a surgical procedure. The system 350 may include a physical anatomical model 348. The physical anatomical model 348 may incorporate any of the features of the physical anatomical models disclosed herein. The physical anatomical model 348 may be representative of a foot. The physical anatomical model 348 may incorporate features representative of one or more defects, such as a bunion.

The physical anatomical model 348 may include one or more model portions 353. In implementations, the model portions 353 may include a first model portion 353-1 and a second model portion 353-2. The first model portion 353-1 may be patient-specific and/or non-reusable. The first model portion 353-1 may be associated with a respective virtual anatomical model 129 (FIG. 2). The second model portion 353-2 may be reusable and may have a construction that may approximate the geometry of anatomy (e.g., ankle). The second model portion 353-2 may not be associated with a particular patient. The first model portion 353-1 may be releasable attached or otherwise secured to the second model portion 353-2.

The physical anatomical model 348 may include one or more components 354 associated with anatomy, including any of the tissue disclosed herein. The components 354 may include one or more bone components 354B and/or soft tissue components 354S. The system 350 may include a light source 356. The light source 356 may be established in the physical anatomical model 348 utilizing any of the techniques disclosed herein. In implementations, the first model portion 353-1 may incorporate the components 354 and/or light source 356.

Figure 6:
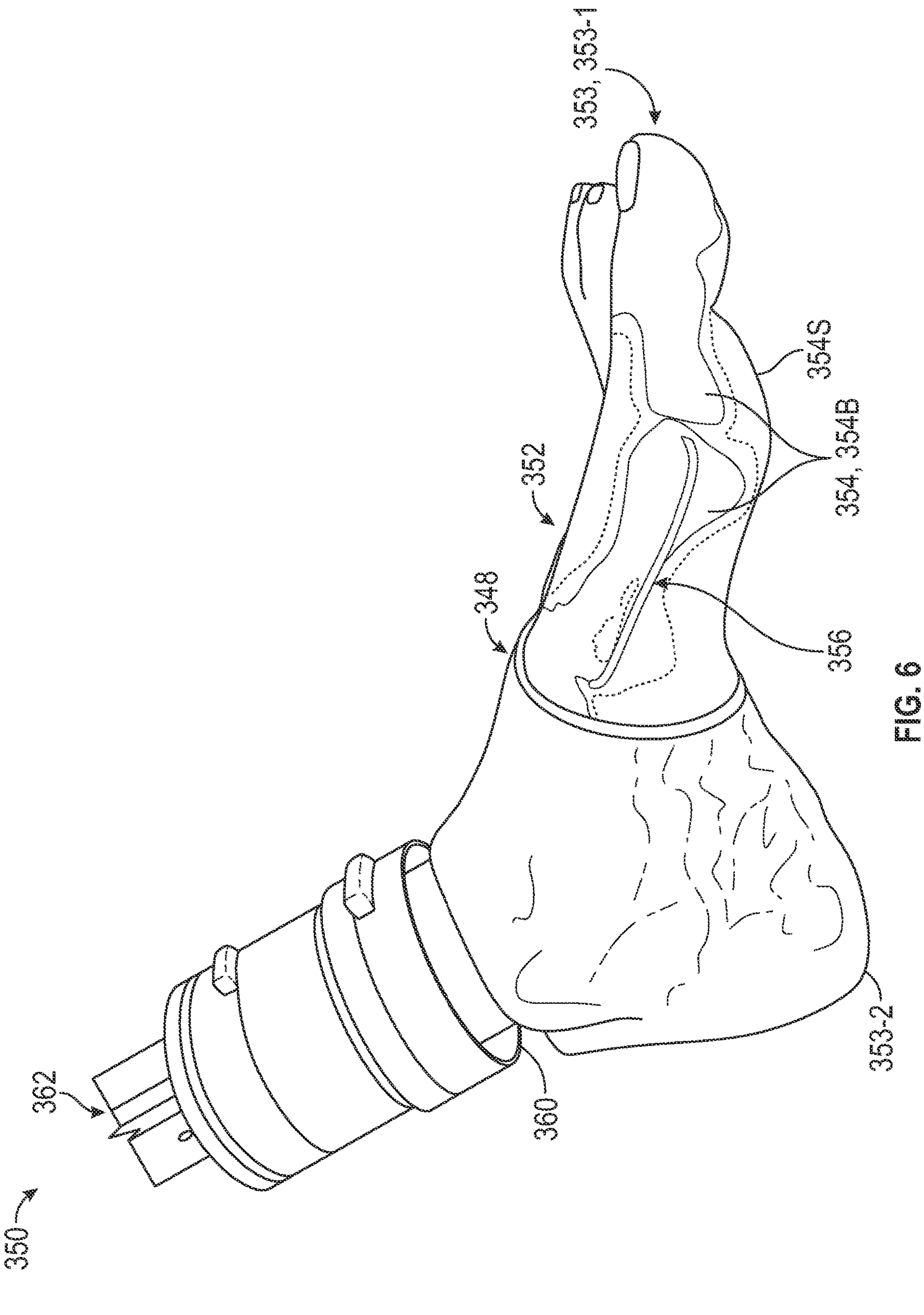
FIG. 6 discloses a perspective view of system of FIG. 5 with the light source in an illuminated mode.

In the implementation of FIG. 5, the light source 356 may be actuated in a first (e.g., non-illuminated) mode. In the implementation of FIG. 6, the light source 356 may be actuated in a second (e.g., illuminated) mode to illuminate the physical anatomical model 348 including the bone component(s) 354B and soft tissue component(s) 354S.

Figure 7:
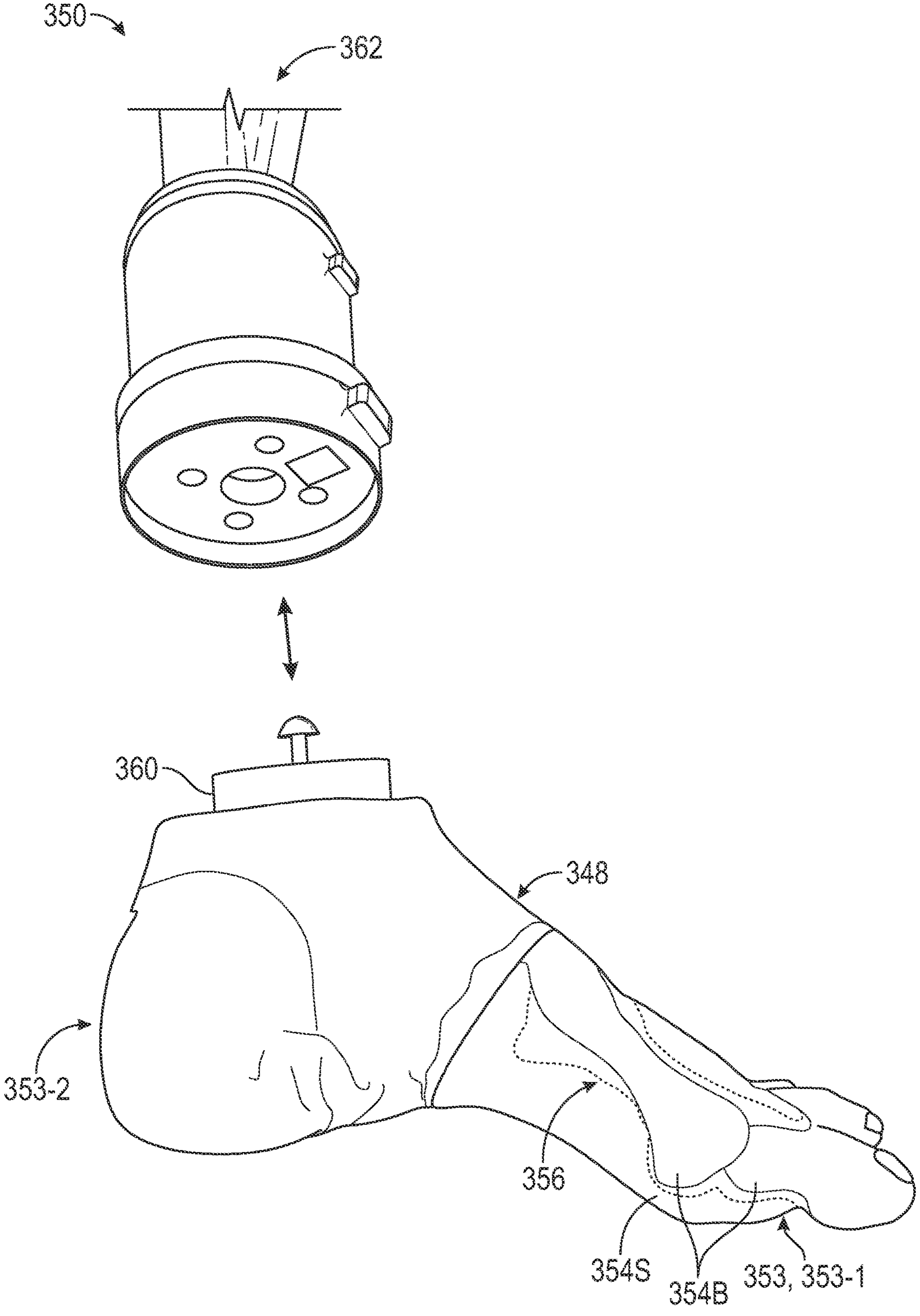
FIG. 7 discloses the physical anatomical model of FIG. 5 disconnected from the positioning fixture.
Figure 8:
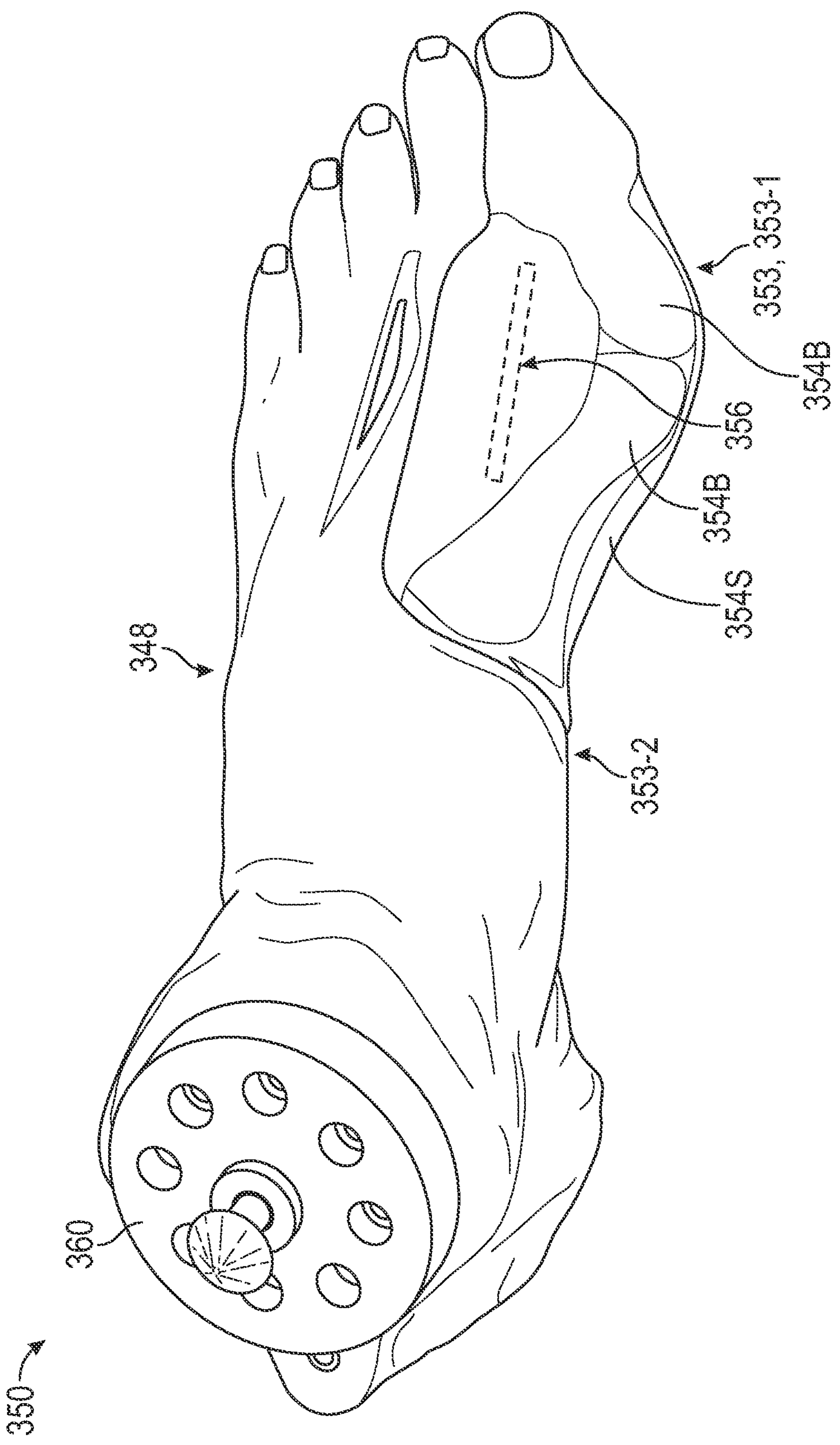
FIG. 8 discloses another view of the physical anatomical model of FIG. 7.

The system 350 may include a mount 360 attached to the main body 352 of the physical anatomical model 348. The mount 360 may be adapted to releasably secure the physical anatomical model 348 to a positioning fixture 362. In implementations, the mount 360 may be fixedly attached or otherwise secured to the second model portion 353-2. The surgeon or clinical user may configure the positioning fixture 362 to position the physical anatomical model 348 at a desired position and/or orientation. FIG. 7 discloses the physical anatomical model 348 disconnected from the positioning fixture 362. FIG. 8 discloses an isolated view of the physical anatomical model 348 disconnected from the positioning fixture 362.

Figure 9:
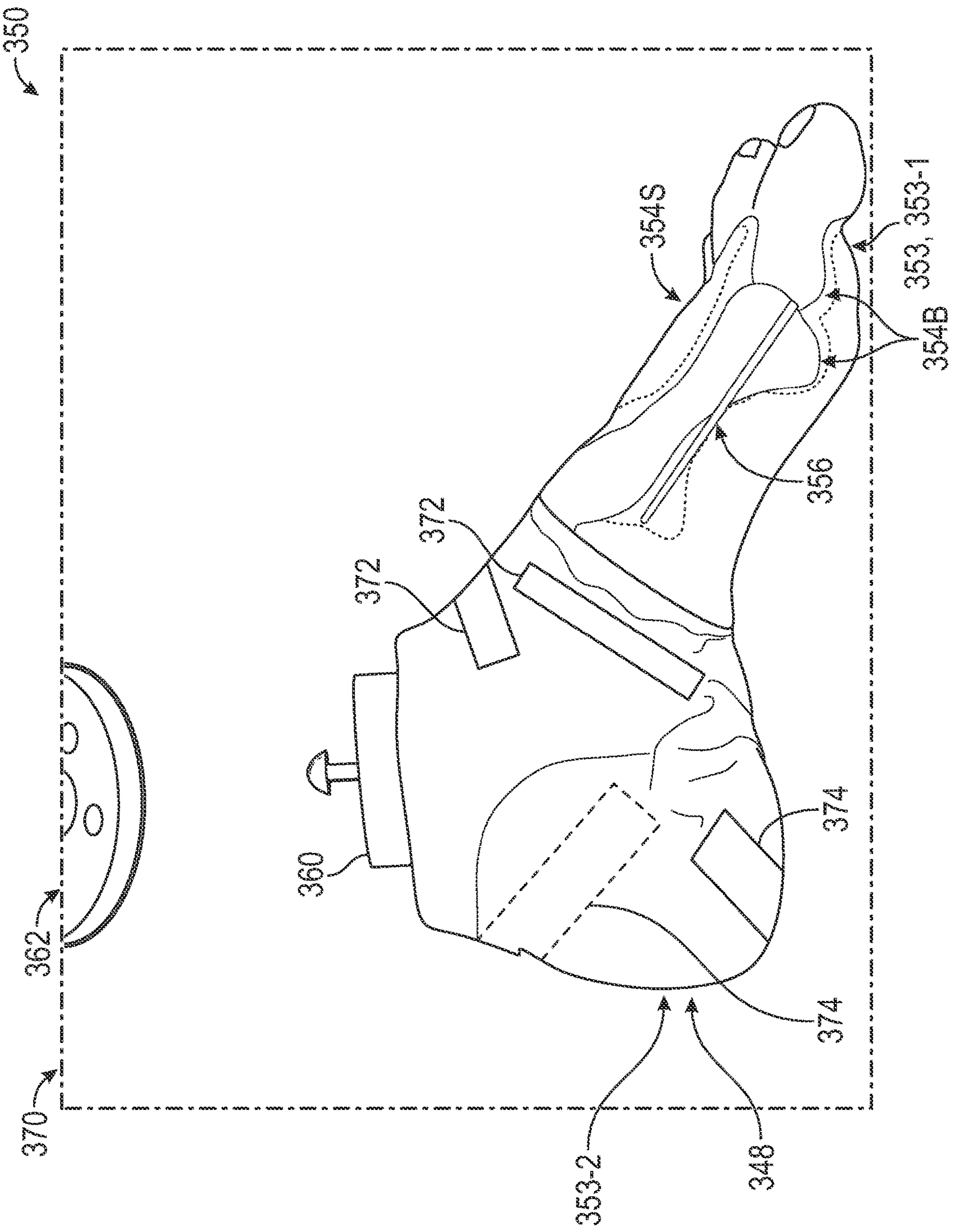
FIG. 9 discloses a side view of the physical anatomical model of FIG. 7 relative to an imaging fixture.
Figure 10:
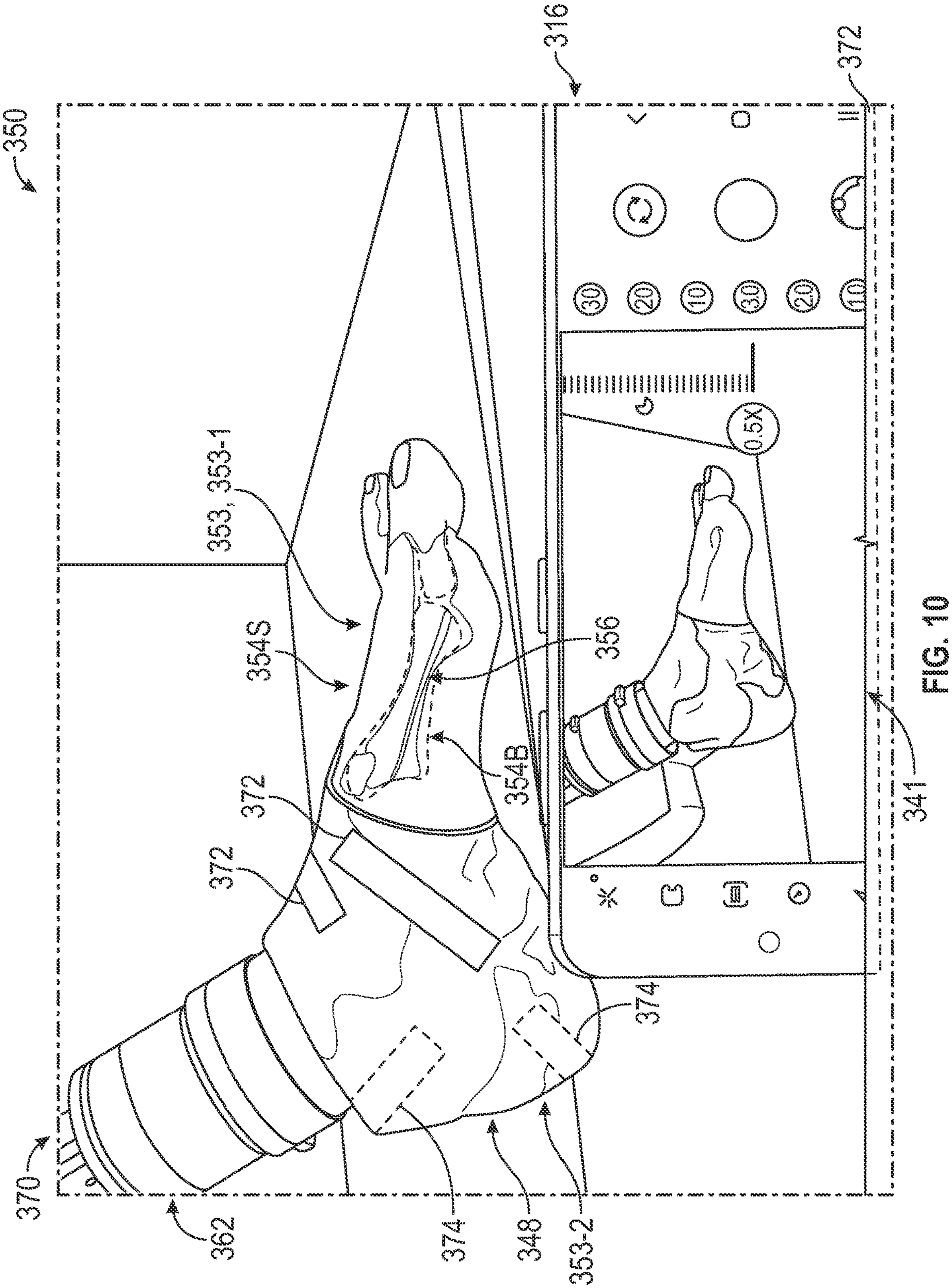
FIG. 10 discloses the physical anatomical model of FIG. 9 coupled to the positioning fixture and positioned relative to an imaging device.

Referring to FIGS. 8-10, with continuing reference to FIGS. 1-8, the surgeon or clinical user may utilize an instrument 364 (FIG. 11) to modify the physical anatomical model 348. The instrument 364 may be a guide or tool such as a drill or saw. The instrument 364 may be utilized to position one or more surgical devices 366 (FIG. 11), such as a guide pin and/or a compression screw or other fastener.

The system 350 may include an imaging device 316. The imaging device 316 may include any of the imaging devices disclosed herein, such as a mobile device including an integrated or external digital camera. The physical anatomical model 348 may be situated relative to the imaging device 316. The imaging device 316 may capture one or more digital images 341 of the physical anatomical model 348. The system 10 (FIGS. 1-2) may receive the digital images 341 and may associated the digital images 341 with the physical anatomical model 348.

The system 350 may include an imaging fixture 370 (shown in dashed lines). The imaging fixture 370 may be dimensioned to engage an imaging device, such as the imaging device 316, such that the imaging device may face the physical anatomical model 348 at a specified orientation. The imaging fixture 370 may include one or more receptacles 372. Each receptacle 372 may be dimensioned to engage an imaging device, such as the imaging device 316. The receptacles 372 may include a plurality of slots arranged at predefined orientations relative to each other for capturing images of the physical anatomical model 348 at the predefined orientations. The predefined orientations may include any of the orientations disclosed herein, such as various planes of the anatomy (e.g., anterior-posterior, lateral, superior-inferior). The surgeon or clinical user may control the imaging device 316 to capture one or more images of the physical anatomical model 348 when the light source 356 is in an illuminated and/or non-illuminated mode. In implementations, the system 350 may include one or more stands 374. The stands 374 may extend from, may be incorporated into and/or may be attached to the physical anatomical model 348. The stands 374 may be dimensioned to support the physical anatomical model 348 and/or engage one or more surgical instruments. The stands 374 may be dimensioned to engage an imaging device, such as the imaging device 316. The stands 374 may be arranged at predefined orientations, including any of the orientations disclosed herein. The stands 374 may be incorporated into the imaging fixture 370. In implementations, the imaging fixture 370 may be omitted.

Figure 12:
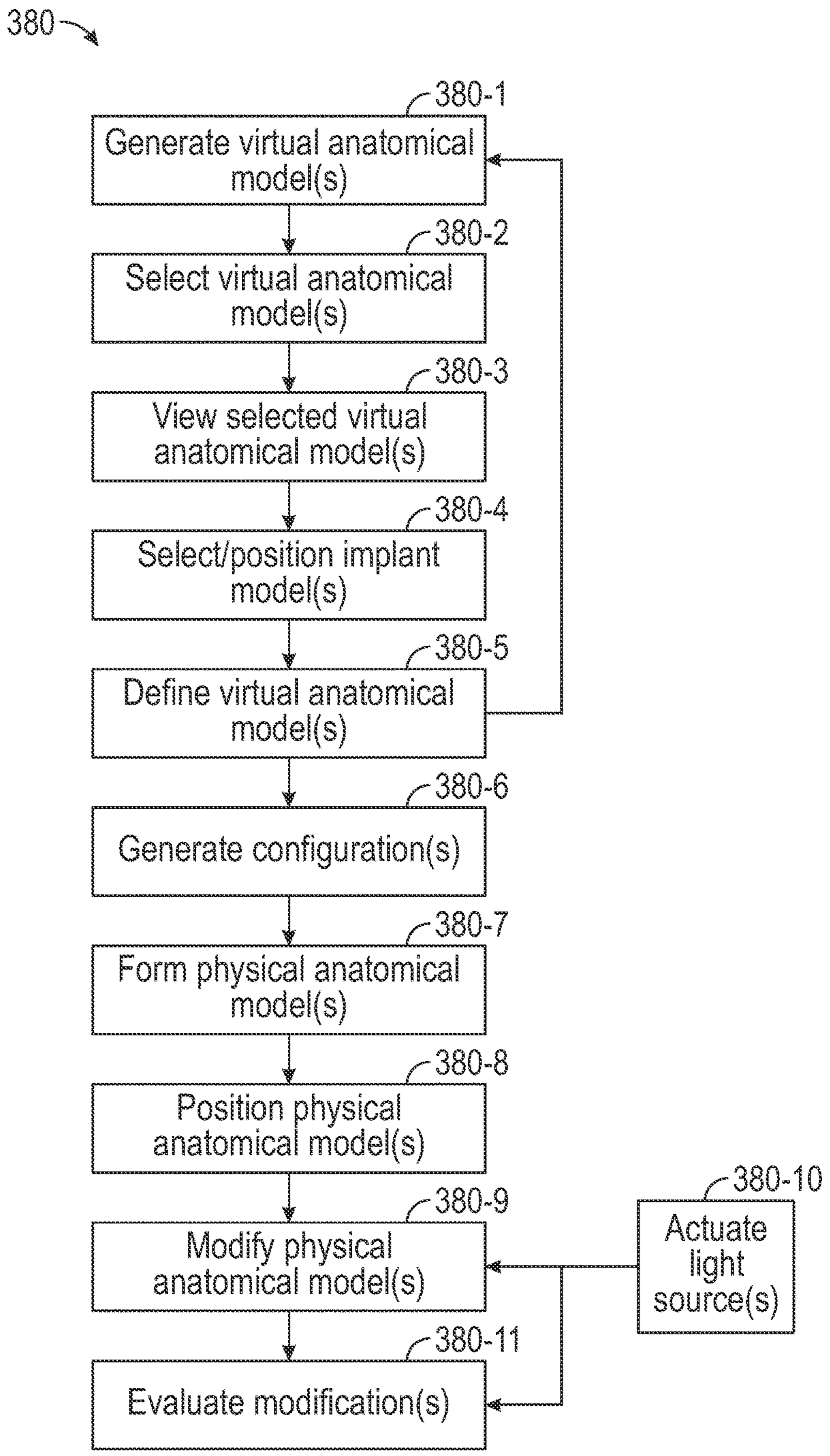
FIG. 12 discloses a method of planning and implementing a surgical procedure.

FIG. 12 discloses a method of planning and performing a surgical procedure in a flowchart 380. The method 380 may be utilized to pre-operatively plan, rehearse and/or train for various surgical procedures, such as an arthroplasty for restoring functionality to shoulders, ankles, feet, knees, hips and other joints having one or more deformities. The method 380 may be utilized with any of the planning systems and virtual and physical anatomical models disclosed herein. The method 380 may be utilized to evaluate the accuracy in which a surgeon implements a surgical procedure on a physical anatomical model associated with an anatomy of a patient. Fewer or additional steps than are recited below could be performed within the scope of this disclosure, and the recited order of steps is not intended to limit this disclosure. Reference is made to the planning system 10 and system 350 including the physical anatomical model 348.

Referring to FIG. 2, with continuing reference to FIG. 12, at step 380-1 one or more virtual anatomical models 129 may be generated or otherwise defined. Each virtual anatomical model 129 may be associated with an anatomy of a patient and may be generated utilizing any of the techniques disclosed herein.

At step 380-2, one or more virtual anatomical models 129 may be selected from a set of virtual anatomical models 129. The virtual anatomical models 129 may be stored in memory of a computing device, such as in the database 128 or the memory 134 of the computing device 132. Selecting the virtual anatomical model 129 may include selecting from various parameters associated with the set of virtual anatomical models 129. The parameters may include any of the parameters disclosed herein, including patient classification, anatomy and/or defect. The parameters may be selected in response to user interaction with the graphical user interface 142. The virtual anatomical models 129 may include any of the anatomies and tissue types disclosed herein, including bone, ligament, tendon, cartilage, etc. At step 380-3, the selected virtual anatomical model(s) 129 may be viewed in the graphical user interface 142.

At step 380-4, one or more implant models 130 may be selected and positioned relative to the selected virtual anatomical model(s) 129. Each implant model 130 may be selected from a set of implant models 130. The implant models 130 may be stored in memory of a computing device, such as in the database 128 or the memory 134 of the computing device 132. The implant models 130 may be associated with any of the implants disclosed herein.

At step 380-5, aspects of one or more of the virtual anatomical models 129 may be defined. Each virtual anatomical model 129 may be defined prior, during and/or subsequent to generating the virtual anatomical model 129 at step 380-1 and/or selecting the virtual anatomical model 129 at step 380-2. Defining the virtual anatomical model 129 may include setting one or more parameters of the virtual anatomical model 129, including any of the parameters disclosed herein. The parameters may be selected in response to user interaction with the graphical user interface 142. The parameters may be associated with one or more indicators I (FIG. 3).

At step 380-6, one or more configurations (e.g., definitions) may be generated. Each configuration may be associated with a physical anatomical model 148 and may be generated utilizing any of the techniques disclosed herein. The configuration may be representative of the selected virtual anatomical model 129. Each configuration may be generated in response to selecting the respective virtual anatomical model 129 at step 380-2 and/or defining the selected virtual anatomical model 129 at step 380-5. The configuration may be established according to the selection or specification of any parameters associated with the selected virtual anatomical model 129. The configuration may include data and other information sufficient to establish a physical anatomical model 148 based on the parameters of the selected virtual anatomical model 129, including coordinate information, moduli of elasticity and color schemes of the associated tissues, etc.

At step 380-7, one or more physical anatomical models 148 may be fabricated or otherwise formed based on the generated configuration 145. Each physical anatomical model 148 may be formed utilizing any of the techniques disclosed herein. The physical anatomical model 148 may be a monolithic structure or may have one or more portions releasably secured to each other.

Figure 13:
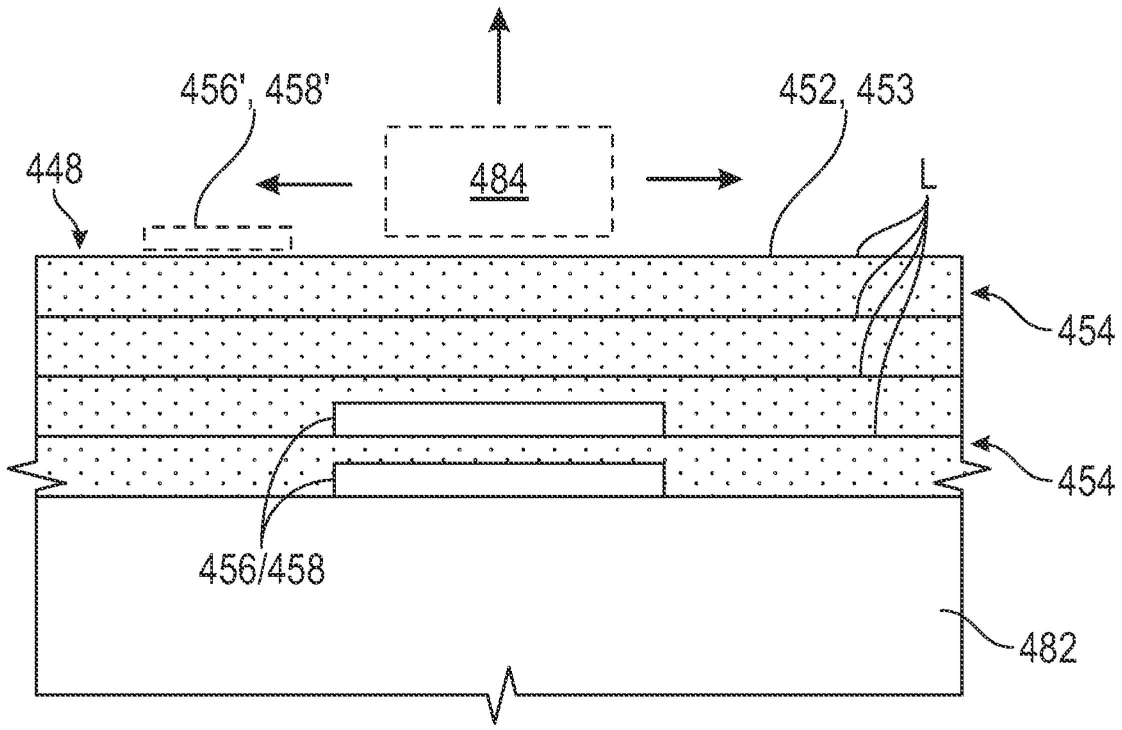
FIG. 13 discloses a system for forming a physical anatomical model.

In the implementation of FIG. 13, one or more layers L of material may be printed or otherwise formed on a substrate 482 to establish a physical anatomical model 448. The physical anatomical model 448 may be representative of a virtual anatomical model 129 (FIG. 2). A device 484 such as a three-dimensional printer may be configured to form the layers L according to data and other information associated with the respective configuration 145 (device 484 shown in dashed lines for illustrative purposes). The layers L of material may include any of the constructions, materials, coloring, textures, porosities, etc. disclosed herein. The layers L may have respective moduli of elasticity that may substantially correspond to moduli of elasticity of respective biomaterial of the anatomy. The porosities of the material forming the physical anatomical model 448 may substantially approximate the porosity or density of the respective tissue.

Step 380-7 may include forming the layers L of material to establish the physical anatomical model 448. The layers L may be formed concurrently and/or sequentially. Each layer L may be homogenous or heterogenous. Heterogenous layers may incorporate different regions associated with respective tissue types, densities, porosities, colors, etc. Step 380-7 may include printing the layers L of material on each other to establish one or more components 454 of the physical anatomical model 448, including any of the components disclosed herein.

The layers L of material may establish a main body 452 of the physical anatomical model 448. The main body 452 may include one or more model portions, one or more bone components and/or one or more soft tissue components. The main body 452 may establish one or more model portions 453. The bone component may have a surface contour representative of a bone. The bone component may include an opaque or translucent material. The soft tissue component may be representative of soft tissue. The soft tissue component may include transparent or translucent material. The layers L of material may have respective moduli of elasticity that may substantially correspond to moduli of elasticity of respective portions of the anatomy.

Step 380-7 may include positioning one or more light sources 456 relative to the physical anatomical model 448. The light sources 456 may include any of the light sources and light modules disclosed herein. The light sources 456 may include one or more light modules 458. The light sources 456 and light modules 458 may be arranged according to any of the teachings disclosed herein. Step 380-7 may include embedding the light source 456 in the main body 452. The layers L of material may be formed such that the model portion 453 and/or physical anatomical model 448 may be a monolithic structure. In implementations, one or more light sources 456' and/or light modules 458' may be positioned along an external surface of the physical anatomical model 448.

At step 380-8, the physical anatomical model 348 may be positioned or otherwise prepared. The physical anatomical model 348 may be secured to one or more positioning fixtures (see, e.g., FIGS. 5-7).

Figure 11:
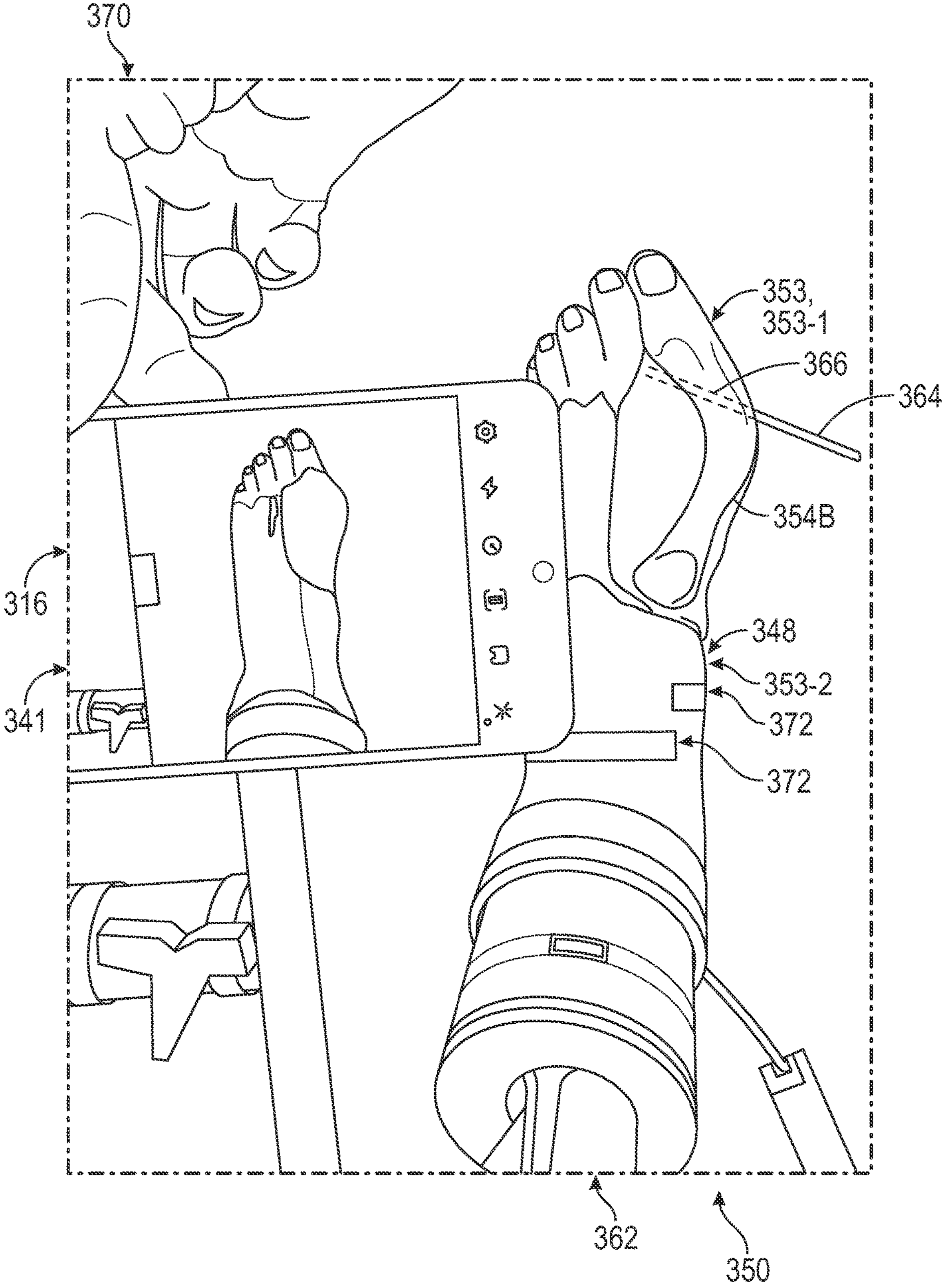
FIG. 11 discloses the physical anatomical model of FIG. 10 in another position relative to an imaging device.

Referring to FIGS. 10-11, with continuing reference to FIG. 12, at step 380-9 one or more modifications to the physical anatomical model(s) 348 may be performed. Step 380-9 may include removing a portion of the physical anatomical model 348 to establish a revised physical anatomical model 348. Various modifications may be performed to simulate surgical operations performed on an anatomy, including any of the modifications disclosed herein such as one or more incision, cutting, drilling, reaming, resection and implantation operations (see, e.g., FIG. 11). Each modification may result in permanently altering a geometry of the physical anatomical model 348.

At step 380-10, one or more light sources 356 may be selectively actuated to illuminate the physical anatomical model 348. Step 380-10 may include actuating the light source 356 in one or more modes. Step 380-10 may include actuating the light source 356 in a first mode to highlight the bone component(s) 354B, but actuating the light source 356 in a second mode to highlight the soft tissue component(s) 354S. The first and second modes may be associated with different frequencies and/or frequency ranges of light generated by the light source 356.

The light source 356 may include a first light module and a second light module (see, e.g., light modules 258-1, 258-2 of FIGS. 3-4). Step 380-10 may include independently actuating the first light module and the second light module to illuminate respective regions of the main body 352 of the physical anatomical model 348. The main body 352 may extend along a first axis (see, e.g. axis X of FIGS. 3-4). The first light module and the second light module may be circumferentially offset from each other relative to the first axis (see e.g., FIGS. 3-4).

At step 380-11, modification(s) to the physical anatomical model(s) 348 may be evaluated utilizing any of the techniques disclosed herein. Step 380-11 may include positioning the physical anatomical model 348 relative to an imaging fixture 370. An imaging device 316 may be positioned in the imaging fixture 370. The surgeon or clinical user may modify the physical anatomical model 348. The surgeon or clinical user may cause the imaging device 316 to capture one or more images 341 of the physical anatomical model 348 when illuminated by the light source 356, including prior to, during and/or subsequent to modification of the physical anatomical model 348. The surgeon or clinical user may cause the imaging device 316 to capture a set of images 341 in one or more positions and orientations relative to the physical anatomical model 348, including any of the positions and orientations disclosed herein. Each set of images 341 may include one or more images 341 capturing illuminated state(s) of the physical anatomical model 348 and/or non-illuminated state(s) of the physical anatomical model 348.

Step 380-11 may include generating a virtual anatomical model 129 (FIG. 2) based on the modified (e.g., revised) physical anatomical model 348. Step 380-11 may include comparing the modified physical anatomical model(s) 348 to a surgical plan 131. In implementations, the modified physical anatomical model(s) may be compared to a predetermined geometry of a virtual anatomical model(s) associated with the surgical plan. Step 380-11 may include generating one or more indicators, including any of the indicators disclosed herein.

The novel devices and methods of this disclosure provide versatility in planning, rehearsing and training for surgical procedures utilizing physical anatomical models. The physical anatomical models may be representative of various anatomy. One or more light sources may be utilized to selectively illuminate the physical anatomical models.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A system for a surgical procedure comprising:
a physical anatomical model including a main body representative of anatomy, the main body comprising:
one or more bone components each having a surface contour representative of a respective bone, wherein the one or more bone components comprise a first material having a material property providing distinct illumination in response to light in a first frequency range;
one or more soft tissue components on the one or more bone components, wherein the one or more soft tissue components are representative of soft tissue and are transparent or translucent, wherein the one or more soft tissue components comprise a second material having a material property providing distinct illumination in response to light in a second frequency range; and
a light source embedded in the main body, wherein the light source is selectively actuatable to communicate light in the first frequency range without communicating light in the second frequency range to highlight the one or more bone components, and the light source is selectively actuatable to communicate light in the second frequency range without communicating light in the first frequency range to highlight the one or more soft tissue components.

2. The system as recited in claim 1, wherein the light source is at least partially embedded in the one or more bone components.

3. The system as recited in claim 1, wherein the light source is situated between the one or more bone components and the one or more soft tissue components.

4. The system as recited in claim 1, wherein the light source includes a first light module and a second light module spaced apart from the first light module, the first and second light modules being independently controllable.

5. The system as recited in claim 4, wherein:
the main body extends along a first axis;
the first light module extends along a first reference plane extending along the first axis;
the second light module extends along a second reference plane extending along the first axis; and
the first and second reference planes are circumferentially offset to establish an angle.

6. The system as recited in claim 5, wherein the first light module and/or the second light module includes an array of light emitting diodes distributed along a respective one of the first and second reference planes.

7. The system as recited in claim 5, wherein:
the angle is approximately 90 degrees or more; and/or
the first reference plane is associated with an anterior-posterior view of the physical anatomical model, and the second reference plane is associated with a lateral view of the physical anatomical model.

8. The system as recited in claim 1, further comprising:
at least one indicator embedded in the main body, the at least one indicator adapted to selectively illuminate in response to the light source.

9. A physical anatomical model for a surgical procedure comprising:
an opaque bone component representative of bone, wherein the bone component comprises a first material having a material property providing distinct illumination in response to light in a first frequency range;
a transparent or translucent soft tissue component representative of soft tissue, wherein the soft tissue component is disposed along a circumference of the bone component, and wherein the soft tissue component comprises a second material having a material property providing distinct illumination in response to light in a second frequency range; and
a light source between the bone component and the soft tissue component, the light source including a plurality of light modules distributed about the circumference of the bone component, wherein the light source is selectively actuatable to communicate light in the first frequency range without communicating light in the second frequency range to highlight the bone component, and the light source is selectively actuatable to communicate light in the second frequency range without communicating light in the first frequency range to highlight the soft tissue component.

10. The physical anatomical model as recited in claim 9, wherein the plurality of light modules are independently controllable.

11. The physical anatomical model as recited in claim 9, wherein the plurality of light modules include a pair of light modules circumferentially offset at angle of approximately 90 degrees or more relative to an axis of the bone component.

12. A method of rehearsing for a surgical procedure comprising:
defining a virtual anatomical model associated with an anatomy;
forming a plurality of layers of material to establish a physical anatomical model representative of the virtual anatomical model, wherein the layers of material establish a main body comprising:
a bone component having a surface contour representative of a bone, the bone component comprising an opaque material having a material property providing distinct illumination in response to light in a first frequency range; and
a soft tissue component representative of soft tissue, the soft tissue component comprising transparent or translucent material having a material property providing distinct illumination in response to light in a second frequency range; and
embedding a light source in the main body, wherein the light source is selectively actuatable to communicate light in the first frequency range without communicating light in the second frequency range to highlight the bone component, and the light source is selectively actuatable to communicate light in the second frequency range without communicating light in the first frequency range to highlight the soft tissue component.

13. The method as recited in claim 12, wherein the layers of material have respective moduli of elasticity that substantially correspond to moduli of elasticity of respective portions of the anatomy.

14. The method as recited in claim 12, further comprising:
actuating the light source to communicate light in the first frequency range but not light in the second frequency range to highlight the bone component, but actuating the light source to communicate light in the second frequency range but not the first frequency range to highlight the soft tissue component.

15. The method as recited in claim 12, wherein the light source includes a first light module and a second light module, and further comprising:
independently actuating the first light module and the second light module to illuminate respective regions of the main body.

16. The method as recited in claim 15, wherein:
the main body extends along a first axis; and
the first light module and the second light module are circumferentially offset from each other relative to the first axis.

17. The method as recited in claim 12, further comprising:
positioning the physical anatomical model relative to an imaging fixture;
positioning an imaging device in the imaging fixture;
modifying the physical anatomical model; and
causing the imaging device to capture one or more images of the modified physical anatomical model when illuminated by the light source.

18. The method as recited in claim 17, further comprising:
comparing the one or more images of the modified physical anatomical model to a surgical plan; and
generating an indicator in response to the comparing step.

19. The system as recited in claim 1, further comprising:
an imaging fixture dimensioned to engage an imaging device such that the imaging device faces the physical anatomical model.

20. The system as recited in claim 8, wherein:
the at least one indicator includes a first indicator associated with a predetermined target zone and a second indicator associated with a predetermined warning zone, and the target zone and the warming zone are associated with a surgical procedure.

* * * * *